United States Patent [19]

Flesher et al.

[11] Patent Number: 5,154,920

[45] Date of Patent: Oct. 13, 1992

[54] DISINFECTANT POLYMERIC COATINGS FOR HARD SURFACES

[75] Inventors: Daniel J. Flesher, St. Paul; Robert T. Hall, Welch, both of Minn.; Richard C. Chromecek, Litchfield, Conn.; Michael C. Braun, Port Jervis, N.Y.

[73] Assignee: Ecolab Inc., St. Paul, Minn.

[21] Appl. No.: 111,100

[22] Filed: Oct. 21, 1987

Related U.S. Application Data

[63] Continuation of Ser. No. 711,189, Mar. 13, 1985, abandoned.

[51] Int. Cl.$^5$ ............................................. A01N 25/24
[52] U.S. Cl. ................................. 514/643; 106/15.05; 514/730; 514/736; 514/737; 514/772.6; 514/772.4
[58] Field of Search .................. 424/81, 78; 106/15.05

[56] References Cited

U.S. PATENT DOCUMENTS

| | | | |
|---|---|---|---|
| 2,873,263 | 2/1959 | Lal | 260/45.4 |
| 2,875,097 | 2/1959 | Pritchard | 117/138.5 |
| 3,370,050 | 2/1968 | Seiner et al. | 260/80.81 |
| 3,576,760 | 4/1971 | Gould et al. | 252/402 |
| 3,577,516 | 5/1971 | Gould et al. | 424/46 |
| 3,881,026 | 4/1975 | Shepherd et al. | 426/223 |
| 3,886,125 | 5/1972 | Chromecek | 260/783 |
| 3,966,902 | 6/1976 | Chromecek | 424/59 |
| 4,483,848 | 11/1984 | Cox et al. | 536/1.1 |
| 4,747,419 | 5/1988 | Flynn | 132/73 |

OTHER PUBLICATIONS

The Merck Index, 10th ed; Merck & Co., Inc. 1983.
Merck Index, 10th ed. (2367) 2983.
Plytrap FLM polymer film system, published by Wickhen Products, Inc. 1984.
An investigation of microbial contamination in the home by Elizabeth Scott, Sally F. Bloomfield and C. G. Barlow.
Evaluation of disinfectants in the domestic environment under in use conditions, by Elizabeth Scott, Sally F. Bloomfield, and C. G. Barlow, accepted Sep. 21, 1983.
A bacterial survey of hygene in the home by Elizabeth Scott, Sally F. Bloomfield, and C. G. Barlow 1983.
"POLYTRAP FLM Polymer Film System", Wickhen Products, Inc., Huguenot, N.Y. brochure (1984).

Primary Examiner—Joseph Paul Brust
Assistant Examiner—M. Gabilan
Attorney, Agent, or Firm—Merchant, Gould, Smith, Edell, Welter & Schmidt

[57] ABSTRACT

Liquid disinfectant compositions are disclosed which can be used to surface-coat substrates with polymeric films which are adherent, water-resistant and which can impart prolonged germicidal properties to the treated surfaces.

25 Claims, No Drawings

DISINFECTANT POLYMERIC COATINGS FOR HARD SURFACES

This is a continuation of application Ser. No. 06/711,189, filed Mar. 13, 1985, now abandoned.

FIELD OF THE INVENTION

The invention relates to liquid compositions that can form adherent, transparent, abrasion resistant polymeric films having prolonged antimicrobial properties.

BACKGROUND OF THE INVENTION

Recent studies have indicated that the contamination of both wet and dry household surfaces with potentially pathogenic quantities of bacteria is widespread. Following a study of bacterial flora in 200 homes, Scott et al., in *J. Hyg. Camb.*, Vol. 89, 279 (1982) concluded that improved decontamination procedures are necessary, particularly at sites which are repeatedly wetted, such as the surfaces of sinks, toilets, draining boards, stoves, washing machines and the like. However, controlled in use tests employing dilute aqueous detergents at kitchen and bathroom sites achieved no observable reduction in microbial contamination, while application of aqueous hypochlorite and phenolic disinfectant compositions only produced a significant reduction in contamination levels for 3-6 hours. In their evaluation of disinfectants in the domestic environment, Scott et al., *J. Hyg. Camb.*, Vol. 92, 193 (1984) hypothesized that the rapid recontamination was due both to re-usage of surfaces such as toilets and to the local multiplication of residual colonies at repeatedly wetted sites such as sinks.

Compositions intended for the controlled release of a disinfectant from a film of a stabilized hydrophilic polymer are disclosed in U.S. Pat. No. 3,966,902. The polymer complex is stabilized as a metal complex by the addition of an inorganic aluminum, zirconium or zinc salt such as aluminum chlorohydrol to the polymerization mixture. The stabilization adjuvant is necessary due to the fact that upon contact with water, films of simple hydrogels become highly swollen and rapidly elute their additives. Furthermore, dry films both simple and metal-complexed hydrogels do not adhere well to ceramic and other hard surfaces and lose their adhesion completely when wetted.

Thus, a need exists for a disinfectant composition capable of forming a polymeric film on hard surfaces such as those formed of ceramics, glass, formica, plastics, metals and the like, which film can entrain a germicidal substance such as a quaternary ammonium salt or a phenolic. A need also exists for a composition capable of yielding a transparent film having strong adhesion to the substrate surface and high resistance against abrasive removal during commonly-employed cleansing procedures. A further need exists for a disinfectant film capable of providing extended protection against microbial contamination.

BRIEF DESCRIPTION OF THE INVENTION

The present invention provides liquid disinfectant compositions which yield adherent, water-resistant, polymeric films when coated onto porous or non-porous hard surfaces and dried. The liquid compositions comprise germicidal agents which are effective to destroy preexisting microbial colonies and which impart prolonged antimicrobial properties to the deposited films.

The liquid disinfectant compositions will comprise a film-forming copolymer of (a) a monomer having a hydrophilic group and (b) an alpha, beta-unsaturated carboxylic acid ester selected from the group consisting of aromatic esters, cycloalkyl esters and mixtures thereof. Preferably the copolymer will comprise about 20–99.5% of the hydrophilic monomer, and about 0.5–80 mol-% of the cycloalkyl or aromatic ester monomer, which can optionally be replaced with about 1–90 mol-% of an alkyl or alkoxy(alkyl) ester of an alpha, beta-unsaturated acid. The copolymers are substantially free of inorganic metal salt complexation agents such as those disclosed in U.S. Pat. No. 3,966,902. These copolymers can be viewed as modified hydrogels which are surprisingly capable of forming films which are adherent to hard surfaces and are resistant to removal when exposed to water and mild abrasion. The films can be readily deposited from dilute solutions or dispersions of the copolymer in volatile solvent systems. These liquid systems will also incorporate germicidal agents such as phenols or a quaternary ammonium salt. The agents are entrapped in the dried polymeric films, and can be incrementally released when the coated surface is contacted with moisture. Contact with atmospheric humidity can assist in maintaining treated surfaces in a substantially microbe-free condition, while exposure to larger amounts of water, as when the surface is moistened by wiping, food residues, dishwater and the like, can lead to the release of increased amounts of the germicide. The polymeric films remain clear and nontacky, and thus do not detract from the appearance of the surfaces to which they are applied.

Although not wishing to be bound by any theory of action, it is believed that the desirable properties of the present composition is due to the balance of hydrophilic and hydrophobic properties of the copolymer. The hydrophilicity of the resultant films may assist both the retention of the germicide and its exposure and activation by externally-applied water. The hydrophobicity imparted to the films by the aromatic and/or the cycloalkyl ester comonomer apparently imparts the necessary adherence and abrasion-resistance to the dried films.

As used herein with respect to antimicrobial action or to the release of a germicide from the present films, the term "prolonged" is intended to refer to the retention of substantial antimicrobial action as determined by laboratory test methods after at least 2 and most preferably after at least 5–10 water washes.

As used herein with respect to the solvents used as carriers for the active ingredients of the present compositions, the term "volatile" is intended to define solvents or solvent systems which readily evaporate when applied to hard surfaces in thin films at ambient conditions e.g. at about 15°–35° C.

As used herein with respect to the surfaces treated by the present compositions, the term "hard" is intended to refer to surfaces composed of refractory materials such as glazed and unglazed tile, brick, porcelain, ceramics, metals, glass and the like, and also includes hard plastics such as formica, polystyrenes, vinyls, acrylics, polyesters, and the like.

Percentages of materials are weight percentages (wt-%) unless otherwise indicated.

DETAILED DESCRIPTION OF THE INVENTION

The liquid disinfectant composition of the present invention comprises a solution of a minor amount of a film-forming copolymer of (a) a monomer having a hydrophilic functional group, and (b) about 0.5–80 mol-% of said copolymer of an alpha, beta-unsaturated carboxylic acid ester selected from the group consisting of aromatic esters, cycloalkyl esters, and mixtures thereof. The copolymer is dissolved in a major amount of a volatile solvent which also incorporates an amount of a germicidal agent effective to impart prolonged antimicrobial properties to the films formed upon removal of the solvent from coatings of said compositions. Copolymer monomer (b) preferably comprises a combination of a cycloalkyl ester or an aromatic ester of an alpha, beta-unsaturated acid in combination with about 1–90 mol-% of the cycloalkyl or aromatic ester of an alkyl ester or an (alkoxy)alkyl ester of an alpha, beta-unsaturated acid.

The Hydrophilic Monomer

Hydrophilic monomer materials which may be utilized in accord with the present invention are preferably esters of alpha, beta-unsaturated carboxylic acids such as methacrylic acid, acrylic acid, itaconic acid, aaconitic acid, cinnamic acid, crotonic acid, mesaconic acid, carboxyethyl acrylic acid, maleic acid, fumaric acid and the like. For example, preferred hydroxylalkyl esters include the esters of these acids and ethylene glycol, di-, tri-, tetra- and (poly)ethylene glycols, propylene glycol and dipropylene glycol; 1,3- or 1,4-butylene glycol; 1,6-hexamethylene glycol, and the like. The preferred unsaturated carboxylic acids include $C_3$–$C_{10}$-carboxylic acids, i.e., acrylic acid, methacrylic acid, and itaconic acid.

Suitable hydrophilic monomers containing amino groups as functional groups include the following: diethylaminoethyl acrylate or methacrylate, dimethylaminoethyl acrylate or methacrylate, monoethylaminoethyl acrylate or methacrylate, tert-butylaminoethyl methacrylate, piperidinoethyl methacrylate, morpholinoethyl methacrylate, dimethylaminopropyl acrylate and methacrylate, 2-pyrrolidinoethyl methacrylate, 3-dimethylaminoethyl-2-hydroxy-propyl acrylate or methacrylate, 2-aminoethyl acrylate or methacrylate, N-methyl acrylamide or methacrylamide, 2-hydroxyethyl acrylamide or methacrylamide, isopropyl-, t-butyl- and t-octylacrylamide or methacrylamide, diacetone acrylamide and the like.

Preferably the film-forming copolymers of the present invention will incorporate about 20–99.5 mol-% of the hydrophilic monomer component, most preferably about 50–95 mol-%.

The Comonomer Modifier

In accord with the present invention, the copolymerization of the hydrophilic monomer with at least one alpha, beta-unsaturated carboxylic acid ester selected from the group consisting of cycloalkyl esters, aromatic esters, and mixtures thereof, substantially improves the adhesion of the copolymer films to hard surfaces. Preferably, the copolymer will include about 0.5–80 mol-% of at least one of these modifying comonomers, most preferably about 1–50 mol-%.

As used herein, the term "cycloalkyl ester" includes bi- and tricycloalkyl esters, and the term "aromatic ester" includes hetero-aromatic esters. Especially preferred cycloalkyl and aromatic esters are those of acrylic acid, methacrylic acid or itaconic acid. Useful aromatic esters of these acids include phenyl, benzyl, tetrahydrofurfuryl, and phenoxyethyl esters. Useful cycloalkyl esters include $C_5$–$C_{12}$ cycloalkyls, e.g. the cyclohexyl, isobornyl and adamantyl esters of these acids.

Alkyl and alkoxy(alkyl) esters of alpha, beta-unsaturated carboxvlic acids can be used in combination with the aromatic and/or cycloalkyl ester. Preferably the alkyl esters will be selected from higher(alkyl) esters, such as those of about 5–22 carbon atoms, most preferably about 5–12 carbon atoms. The alkyl and alkoxy (alkyl) esters can be employed to the extent of about 1–90 mol-% by weight of the total of the modifying comonomer. Preferably the mol-% ratio of cycloalkyl or aromatic ester to alkyl ester is about 2:1–1:2.

The alkyl and (alkoxy)alkyl esters of acrylic acid, methacrylic acid and itaconic acid are preferred for use in the present comonomer mixtures.

Examples of these fatty-alkyl ester comonomers which can be employed in combination with cycloalkyl and/or aromatic ester monomers include myristyl, palmityl and stearyl acrylates, methacrylates and itaconates.

Examples of useful $C_5$–$C_{12}$ compounds include hexyl, octyl, ethyl(hexyl), isodecyl and lauryl, acrylates, methacrylates and itaconates. Alkyl esters having branched, as opposed to straight chain moieties are also preferred for use in the present copolymers.

(Alkoxy)alkyl esters useful as comonomers include ($C_1$–$C_4$)alkoxy($C_1$–$C_4$-alkyl) esters of acrylic, methacrylic or itaconic acid such as (methoxy)ethyl, (ethoxy)ethyl, (methoxy)propyl, (ethoxy)propyl and the like.

The Polymerization Reaction

The film-forming copolymers can be prepared by carrying out the polymerization of the monomers in a solvent or solvent mixture and at concentrations wherein the resultant copolymers remain in solution. Preferred solvents include lower alkanols such as ethanol; ketones, glycol esters or ethers, lower(alkyl)acetates; tetrahydrofuran, dimethylformamide and the like. The monomeric starting materials are typically dissolved in the solvent to the desired concentration, e.g. to a total concentration about 15–30% by weight, although higher or lower concentrations may be employed in some cases.

The polymerization reactions are initiated in the conventional manner and preferably by use of radical-forming initiators. Instances of suitable initiators include dibenzoyl peroxide, tert-butyl peroctoate, cumene hydroperoxide, diazodiisobutyrodinitrile, diisopropylpercarbonate, ammonium persulfate, and the like, per se or in combination with a reducing agent, i.e., in the form of an oxidation-reduction system.

During the course of the reaction, the reaction mixture may be agitated and heated, preferably in a closed system under an inert atmosphere, to about 50°–100° C., preferably to about 75°–95° C. After completion of the polymerization reaction, a solution of copolymer results, which can be employed without further purification or concentration in the present disinfectant compositions.

The Germicidal Agent

The liquid compositions will incorporate an amount of one or more germicidal agents effective to both disinfect surfaces upon contact and to impart prolonged antimicrobial action to the polymeric films prepared therefrom. A wide variety of antimicrobial agents may be included in effective amounts without inducing undesirable interactions or chemical reactions between the major components of the compositions. Such agents can include chlorhexidine, chlorhexidine gluconate, glutaral, halazone, hexachlorophene, nitrofurazone, nitromersol, povidone-iodine, thimerosol, $C_1-C_5$-parabens, hypochlorite salts, clofucarban, clorophene, poloxamer-iodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl) (diethylenediamine)glycine and/or (dodecyl)(aminopropyl) glycine and the like.

Phenolic compounds are among the preferred germicides for use in the present compositions. Useful phenolic germicides include phenol, 2-benzyl-4-chlorophenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-buty-phenol and o-benzyl-p-chlorophenol. The biologically-active, water soluble salts of these compounds may also be employed, e.g., the alkali metal salts. Of these compounds o-benzyl-p-chlorophenol is preferred due to its high germidical power.

Quaternary ammonium salts are also preferred germicides for use in the present invention and include the N-(higher) $C_{14}-C_{24}$-alkyl-N-benzyl-quaternary ammonium salts which comprise water solubilizing anions such as halide, e.g., chloride, bromide and iodide; sulfate, methosulfate and the like and the heterocyclic imides such as the imidazolinium salts.

For convenience, the aliphatiac quaternary ammonium salts may be structurally defined as follows:

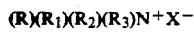

$$(R)(R_1)(R_2)(R_3)N^+X^-$$

wherein R is benzyl, or lower(alkyl) benzyl; $R_1$ is alkyl of 10 to 24, preferably 12 to 22 carbon atoms; $R_2$ is $C_{10}-C_{24}$-alkyl, $C_1-C_4$-alkyl or $C_1-C_4$-hydroxyalkyl, $R_3$ is lower alkyl or hydroxyalkyl of 1 to 4 carbon atoms and X represents an anion capable of imparting water solubility or dispersibility including the aforementioned chloride, bromide, iodide, sulfate and methosulfate. Particularly preferred species of these aliphatiac quats include n-$C_{12}-C_{18}$-alkyl-dimethylbenzylammonium chloride (myrisalkonium chloride), n-$C_{12}-C_{24}$-alkyldimethyl (ethylbenzyl) ammonium chloride (quaternium 14), dimethyl(benzyl)ammonium chloride and mixtures thereof. These compounds are commercially available as the BTC series from Onyx Chemical Co., Jersey City, N.J. For example, BTC 2125M is a mixture of myrisalkonium chloride and quaternium-14.

Other useful aliphatic quaternary ammonium compounds include the N,N-di-(higher)-$C10-C_{24}$-alkyl-N,N-di(lower)-$C_1-C_4$-alkyl-quaternary ammonium salts such as $C_{10-20}$N-alkyl-(dimethyl)-benzyl ammonium salt including distearyl(dimethyl)ammonium chloride, cetyl(dimethyl)ethyl ammonium bromide, dicoco(dimethyl)ammonium chloride, dihydrogenated tallow(dimethyl)ammonium chloride, di-tallow-(dimethyl)ammonium chloride, distearyl(dimethyl) ammonium methosulfate cetyl(trimethyl)ammonium bromide and di-hydrogenated-tallow(dimethyl)ammonium methosulfate.

Other useful nitrogenous germicides include benzethonium chloride, cetylpyridinium chloride, methylbenzethonium chloride, domiphen bromide, gentian violet, and the like.

The total concentration of the germicidal component of the present liquid compositions can vary widely, depending upon its antimicrobial activity, solubility, stability and the like. Although high weight ratios of germicide to copolymer, e.g. 2-3:1, can afford satisfactory disinfectant films, generally the concentration of the germicide will not exceed the concentration of the dissolved copolymer. For example, the present disinfectant compositions will preferably comprise about 0.01-10%, most preferably about 0.05-5% by weight of the phenolic or quaternary ammonium salts. Highly durable, abrasion resistant films can be achieved when the total concentration of the germicidal agent in the present compositions comprises about 0.01-50%, preferably about 0.25-20%, and most preferably about 0.5-5% by weight of the dissolved copolymer.

Preparation and Application of the Compositions

The present film-forming liquid compositions are readily prepared by dissolving the germicidal agent in a solution of the copolymer with agitation under ambient conditions, followed by dilution of the resultant solution to the appropriate concentration by addition of the volatile carrier solvent or solvent system. Since the copolymer is commonly prepared in a volatile solvent such as a lower(alkanol) or a lower(alkyl)acetate, this solution can be diluted with a compatible organic solvent. As the organic solvent there can be employed alcohols, particularly lower aliphatic saturated alcohols, e.g. $C_{1-4}$alkanol, ethyl alcohol, isopropyl alcohol, propyl alcohol, glycols, e.g. ethylene glycol diethylene glycol, propylene glycol and dipropylene glycol, ethylene glycol methyl ether, ethylene glycol ethyl ether, n-propylene glycol monomethyl ether, n-propylene glycol monoethyl ether, isopropylene glycol monomethyl ether, isopropylene glycol monoethyl ether, m-pyrol and ethyl acetate. Mixtures of these solvents with amounts of water can also be used, provided that the homogeneous solutions of the copolymer and the germicide are maintained. For example solutions formed by dissolving the germicide in ethanolic solutions of the comonomer can be diluted with a compatible volatile solvent or solvent system such as a $C_{1-4}$ alkanol plus water including isopropanol (isopropyl alcohol) or isopropanol-water. Useful compositions of this type can comprise at least about 85% of a $C_{1-4}$ alkanol or a $C_{1-4}$ alkanol and water such as isopropanol or a mixture of isopropanol and water.

Therefore, the preferred liquid disinfectant compositions of the present invention will comprise about 0.25-10%, preferably about 0.5-5% of the film-forming copolymer; about 0.10-10%, preferably about 0.05-5% of the germicidal agent, most preferably selected from a phenolic or quaternary ammonium salt; the remainder of the composition being the volatile solvent or solvent-system.

Preferably the film-forming copolymer will incorporate about 50-95 mol-% of the hydrophilic monomer, most preferably 2-hydroxyethylmethacrylate or 2-hydroxyethylacrylate; and about 10-35 mol-% of a $C_5-C_8$-cycloalkyl acrylate or methacrylate, an aromatic acrylate or methacrylate or mixtures thereof. Optionally, a higher(alkyl)acrylate or methacrylate monomer will also be included in the copolymer, replacing the cycloalkyl and/or aromatic monomer to the extent of about 25-75 mol-%. Minor amounts of adjuvants such as an indicator of germicide level, fragrance, surfactants, dyes and the like may also be included in the present compositions, insofar as they are compatible with the film-forming process. For example, about 0.5-5% of a compatible surfactant can be included in the present compositions to enhance their cleaning power.

Alternatively a preferred antimicrobial film-forming liquid disinfectant composition can contain, in the absence of other compositions that will materially affect the novel and nonobvious characteristics of the film, a volatile solvent, an amount of a germicidal agent effective to impart prolonged antimicrobial properties to the film, and a minor amount of a film-forming copolymer containing (a) about 50-95 mol-%, based on said copolymer, of a hydrophilic monomer selected from the group consisting of 2-hydroxyethyl-methacrylate, 2-hydroxypropylmethacrylate, 3-hydroxypropyl-methacrylate, and diacetone acrylamide, (b) about 1-10 mol-%, based on said copolymer, of an aromatic or cycloalkyl ester of an alpha, beta-unsaturated $C_{3-10}$ carboxylic acid, and (c) about 1-10 mol-%, based on said copolymer, of a $C_{5-20}$ alkyl ester or an (alkoxy)alkyl ester of an alpha, beta-unsaturated acid.

The finished disinfectant compositions are homogeneous liquids which are applied to the surfaces to be treated by dipping, spraying, brushing, roller coating, pad coating or using similar coating procedures. For household applications, hand-operated pump-type or pressurized aerosol sprayers are effective. Although the present compositions are particularly adapted to adhere to hard surfaces, they can also be employed to coat or otherwise treat materials such as sponges, flexible plastics, textiles, wood and the like. Generally, the coating process is used to disinfect and impart prolonged germicidal properties to a hard porous or nonporous surface by coating said surface with the antimicrobial composition of the invention, removing the solvent from said coating to form a germicidal, water resistant polymeric film, which coating process is continued to the extent required to deliver an amount of the liquid composition which rapidly dries to a clear, uniform polymeric film under ambient conditions, e.g., about 10-100 mg/in$^2$ of liquid composition is generally effective to disinfect and impart prolonged antimicrobial protection to tile surfaces. The germicidal films are glossy, resistant to mild abrasion and are not broken or substantially depleted of biocide by repeated wettings. Repeated application of the liquid compositions does not result in film build-up since the solvents present can act to resolubilize and level the prior-applied film.

The invention will be further described by reference to the following detailed examples.

EXAMPLE 1

Copolymer Preparation

Cyclohexylmethacrylate, 5 mol-% (2.46 g), isodecyl methacrylate, 5 mol-% (3.31 g) and 2-hydroxyethyl methacrylate 90 mol-% (34.23g) were dissolved in 160 ml of 95% ethyl alcohol and 0.4 g of dibenzoyl peroxide were added. The solution was bubbled with nitrogen for 10 minutes and heated in a closed system (pressure bottle) for 8 hours at 80° C. The resulting solution of the copolymer was used for the preparation of disinfectant compositions.

EXAMPLE 2

Copolymer Preparation

A copolymer solution was prepared by the procedure of Example 1, with the exception that 3.0 mol-% cyclohexyl methacrylate, 7 mol-% isodecyl methacrylate and 90 mol-% 2-hydroxyethylmethacrylate were copolymerized.

EXAMPLE 3

Copolymer Preparation

A copolymer solution was prepared by the procedure of Example 1, except that 7.0 mol-% cyclohexyl methacrylate, 3 mol-% isodecyl methacrylate and 90 mol-% 2-hydroxyethyl methacrylate were employed.

EXAMPLE 4

Evaluation of Copolymer Film Adhesion

Films of copolymers were cast from solutions prepared according to Examples 1-3 on glazed ceramic bathroom tiles and formica. After drying at ambient temperatures and humidities, the quality of the glossy films was tested. The appearance of the film and the abrasion caused by the application of a wet paper towel after the coated substrate had been immersed for 45 minutes in water were visually evaluated.

TABLE I

| Copolymer | Film Evaluation | | | |
|---|---|---|---|---|
| | On Tile | | On Formica | |
| Soln | Appearance | Abrasion | Appearance | Abrasion |
| Example 1 | Clear | None | Clear | None |
| Example 2 | Clear | None | Clear | None |
| Example 3 | Clear | None | Clear | None |

The results summarized on Table I indicate that polymeric films cast from alcohol-water (95:5) solutions of the copolymers of Examples 1-3 exhibit satisfactory physical properties when applied to hard surfaces and subsequently exposed to moisture.

EXAMPLE 4

According to the procedure in Example 1, copolymers containing the following hydrophobic cyclic and aliphatic methacrylates can be prepared:
Benzyl methacrylate
Tetrahydrofurfuryl methacrylate
2-Ethylhexyl methacrylate
Isodecyl methacrylate
Lauryl methacrylate
Stearyl methacrylate
Hexyl methacrylate
Phenoxyethyl methacrylate
Isobornyl methacrylate 5 to 50 mol-% of these monomers and/or combinations thereof within these molar limits can be polymerized with 95 to 50 mol% of hydrophilic comonomers such as 2-hydroxyethyl methacrylate, 2- or 3-hydroxypropyl methacrylates and diacetone acrylamide. In each instance in which an aromatic comonomer was employed alone or in admixture with an alkyl ester comonomer, adhesion to the ceramic tiles and the formica is achieved.

EXAMPLE 5

Two-Component Copolymeric Films

Copolymer solutions prepared according to the procedure Example 1 which contained only 2-hydroxyethyl methacrylate and a single cycloalkyl, alkyl or aromatic methacrylate were prepared and their films on tiles and formica were evaluated by the procedures of Example 4.

TABLE II

| | Copolymer Films | | | |
|---|---|---|---|---|
| | On Glazed Tile | | On Formica | |
| Copolymers/Mol % | Appearance | Abrasion | Appearance | Abrasion |
| THFM/10 - HM/90 | C | N | C | S |
| THMM/20 - HM/80 | C | N | C | S |
| IBOM/10 - HM/90 | C | N | C | S |
| IBOM/20 - HM/80 | C | N | C | P |
| BEM/10 - HM/90 | C | N | C | P |
| BEM/20 - HM/80 | C | N | C | P |
| CHM/10 - HM/90 | C | N | C | P |
| CHM/20 - HM/80 | C | N | C | P |
| LM/10 - HM/90 | C | S,P | C | S |
| LM/20 - HM/80 | C | S,P | C | S |
| STEM/10 - HM/90 | C | S,P | C | P |
| STEM/20 - HM/80 | C | S,P | C | P |
| ISDM/10 - HM/90 | C | S,P | C | N |
| ISDM/20 - HM/80 | C | S,P | C | N |
| HEXM/10 - HM/90 | C | S,P | C | N |
| HEXM/20 - HM/80 | C | S,P | C | N |

Monomer Abbreviations

DAA—Diacetone Acrylamide; HM—2-Hydroxyethyl methacrylate; HPM—2-Hydroxypropyl methacrylate; STM—Stearyl methacrylate; LM—Lauryl methacrylate; ISDM—Isodecyl methacrylate; THFM—Tetrahydrofurfuryl methacrylate; IBOM—Isobornyl methacrylate; BEM—Benzyl methacrylate; CHM—Cyclohexyl methacrylate; HEXM—Hexyl methacrylate; MA—Methacrylic acid.

Abbreviations for film Evaluation

H—Hazy; C—Clear; P—Peels off; S—Soft, scratches; N—None.

The copolymers containing only a cycloalkyl or aromatic ester comonomer performed well on tiles but only weakly adhered to formica. Copolymers comprising $C_{11}$–$C_{18}$-alkyl comonomers exhibited satisfactory adhesion to formica but performed poorly on tiles. Copolymers comprising only a $C_6$- or $C_{10}$-ester as the comonomer performed poorly in this evaluation.

EXAMPLE 6

Hydrogel Films

Solutions containing only polymerized hydrophilic monomers were prepared according to the procedure in Example 1, to evaluate the effect of eliminating other comonomers. Films were cast and their adhesion and abrasion resistance to glazed tiles and formica were evaluated after a 45 min. immersion in water.

TABLE III

| | Homopolymeric Films | |
|---|---|---|
| Polymer/Mol % | Appearance | Abrasion by Paper Towel |
| DAA/100 | H | P |
| HM/100 | H | P |
| HPM/100 | H | P |
| MA/100 | C | P |

As indicated by the data summarized in Table III, typical hydrophilic polymers like DAA and HM exhibited high swelling, to yield often hazy films which peeled off the substrates.

EXAMPLE 7

Film-Forming Disinfectant Compositions

A. Preparation of Coated Tiles

Two film-forming liquid disinfectant solutions were prepared by combining the copolymer solution of Example 1 with either a quaternary ammonium salt germicide ("quat"—a mixture of myristyl(dimethyl)(benzyl)ammonium chloride and dodecyl(dimethyl)(p-ethylbenzyl) ammonium chloride, BTC 2125 M ®—80% active, Onyx Chemical Co., Jersey City, N.J., or a phenol (2-benzyl-4-chlorophenol) germicide, and isopropanol, as indicated on Table IV. Films of the disinfectant composition were cast onto glazed and unglazed ceramic tiles to the extent indicated by spraying the tiles with the liquid compositions and allowing the wet coatings to air dry. Clear, abrasion-resistant polymeric films resulted.

TABLE IV

| Disinfectant Compositions | | | |
|---|---|---|---|
| Weight Percent in Formulation | | | |
| Copolymer Solution | Quat | Phenol | iPrOH |
| 9.6 | 3.8 | — | 86.6 |
| 9.6 | — | 3.8 | 86.6 |
| 9.6 | 3.8 | — | 86.6 |
| 9.6 | — | 3.8 | 86.6 |
| 4.9 | 0.49 | — | 43.9+ |

| | | Coated Tiles | | |
|---|---|---|---|---|
| Tile | Formula On | Treated | $Mg/in^2$ on tile of: | |
| Type | Tile (g) | Tile Area | Formula | Germicide |
| Glazed | 0.7 | 16 $in^2$ | 44.0 | 1.3 |
| Glazed | 0.7 | 16 $in^2$ | 44.0 | 1.7 |
| Porous | 0.9 | 11.4 $in^2$ | 79.0 | 2.4 |
| Porous | 0.8 | 11.4 $in^2$ | 79.0 | 2.7 |
| — | — | — | — | — |

+Composition also incorporated 49.41% water and 1.3% nonoxynol-9 (nonionic surfactant).

B. Evaluation of Bacteriostatic Action-Single Inoculation

One ml of a bacterial inoculum (E. coli, $2.6 \times 10^7$ CFU/ml) was spread on each of five tiles coated with the four compositions as indicated in Table IV. Five uncoated glazed and five uncoated porous (unglazed) ceramic tiles were used as controls. Each tile was sprayed with water daily for five days and allowed to air-dry. When dry, rodac contact agar plate sampling of one "new" tile not previously sampled was performed. Previously sampled tiles were resampled. Thus, on the fifth date of testing, one tile had been sampled five times, one four, one three, etc. The results of this testing are summarized on Table V.

TABLE V

| | | Bacteriostatic Film Evaluation | | | | | | | | | | | |
|---|---|---|---|---|---|---|---|---|---|---|---|---|---|
| | | Rodac Sample (CFU Recovered) | | | | | | | Rodac Sample (CFU) | | | | |
| Tile # | Type | 1 | 2 | 3 | 4 | 5 | Tile # | Type | 1 | 2 | 3 | 4 | 5 |
| 1 | Glazed/ | 0 | 0 | 1 | 0 | 0 | 1 | Porous/ | 1 | 0 | 0 | 0 | 0 |
| 2 | Quat | | 1 | 0 | 1 | 0 | 2 | Quat | 3 | 1 | 2 | 2 | 1 |
| 3 | | | | 6 | 0 | 0 | 3 | | | 2 | 2 | 2 | 0 |
| 4 | | | | | 1 | 0 | 4 | | | | | 3 | 1 |
| 5 | | | | | | 2 | 5 | | | | | | 2 |
| 1 | Glazed/ | 0 | 0 | 0 | 1 | 0 | 1 | Porous/ | 2 | 1 | 0 | 2 | 0 |
| 2 | Phenol | | 0 | 0 | 0 | 1 | 2 | Phenol | 0 | 0 | 0 | 2 | 0 |
| 3 | | | | 1 | 0 | 0 | 3 | | | | 3 | 2 | 1 |
| 4 | | | | | 0 | 1 | 4 | | | | | 5 | 1 |
| 5 | | | | | | 1 | 5 | | | | | | 24 |
| 1 | Glazed/ | 5 | 1 | 19 | 21 | 61 | 1 | Porous/ | 1 | 0 | 1 | 0 | 2 |
| 2 | Control | | 8 | 22 | 90 | 32 | 2 | Phenol | | 9 | 17 | 12 | 0 |
| 3 | | | | 8 | 13 | 14 | 3 | | | | 50 | 21$^a$ | 0 |
| 4 | | | | | 13 | 44 | 4 | | | | | 322$^b$ | 5 |

$^a$3 mold colonies also present.
$^b$4 mold colonies also present.

The results summarized on Table V demonstrate that films prepared from the formulations of Table IV are effective in reducing a subsequently-introduced bacterial population. Recovery of bacteria from the control tiles was continuous from day one to day five. Recovery from the treated tiles was not observed or was consistently lower, indicating a static activity situation. The disinfectant films were somewhat less effective on porous than on glazed tiles.

C. Evaluation of Bacteriostatic Action-Multiple Inoculation

The film-forming compositions summarized on Table VI were prepared and employed to cast disinfectant films on glazed tiles (16 in$^2$) as described in Example VII(A).

TABLE VI

| Disinfectant Compositions | | | | | | |
|---|---|---|---|---|---|---|
| Weight Percent in Formula | | | | Coated Tiles | | |
| Copolymer | | | | | Mg/in$^2$ | |
| Solution | Quat | Phenol | i-ProH | Tile | Formula | Germicide |
| 9.6* | 3.8 | — | 86.6 | A | 38.0 | 1.1 |
| 9.6* | — | 3.8 | 86.6 | B | 44.0 | 1.6 |
| 8.9+ | 3.6 | — | 86.6 | C | 38.0 | 1.1 |
| 9.4+ | — | 3.7 | 86.6 | D | 38.0 | 1.4 |

*Solution of Ex. 1.
+Solution of Ex. 2.

Treated and untreated (control) tiles were inoculated with either E. coli or S. aureus (18-24 hr. broth cultures, 10$^6$ CFU/ml) and allowed to air dry. A one inch square sterile cloth swatch was moistened in sterile saline and employed to rub the tile surface in four back and forth motions. The cloth was placed into Letheen broth for enumeration of surviving organisms. The tiles were washed (sampled) daily for 14 days with reinoculation at days 5, 7, 9 and 11. The results of this evaluation are summarized in Table VII.

TABLE VII

| | Prolonged-Release Films Coated Tiles of Table VI | | | | |
|---|---|---|---|---|---|
| Day | Quat (A) | Quat (C) | Phenol (B) | Phenol (D) | Control |
| | E. Coli inoculations | | | | |
| 1* | 0 | 0 | 3 | 15 | 2 |
| 2 | 0 | 0 | 0 | 0 | 1 |
| 3 | 0 | 0 | 0 | 0 | 0 |
| 4 | 0 | 0 | 3 | 1 | 0 |
| 5* | 2 | 2 | 1 | 1 | 74 |

TABLE VII-continued

| | Prolonged-Release Films Coated Tiles of Table VI | | | | |
|---|---|---|---|---|---|
| Day | Quat (A) | Quat (C) | Phenol (B) | Phenol (D) | Control |
| 6 | 0 | 0 | 0 | 1 | 0 |
| 7* | 0 | 0 | 16 | 4 | 1 |
| 8 | 0 | 0 | 0 | 0 | 0 |
| 9* | 0 | 0 | 1 | 1 | 0 |
| 10 | 1 | 0 | 1 | 0 | 0 |
| 11* | 0 | 0 | 0 | 1 | 930 |
| 12 | 0 | 0 | 0 | 0 | 2 |
| 13 | 0 | 0 | 1 | 11 | 29 |
| 14 | 0 | 0 | 0 | 0 | 0 |
| | S. aureus inoculations | | | | |
| 1* | 1 | 0 | 38 | 18 | 395 |
| 2 | 3 | 0 | 8 | 2 | 474 |
| 3 | 1 | 0 | 0 | 0 | 35 |
| 4 | 0 | 0 | 0 | 0 | 3 |
| 5* | 0 | 0 | 40 | 53 | 19000 |
| 6 | 0 | 0 | 0 | 1 | 0 |
| 7 | 0 | 0 | 6 | 0 | 1000 |
| 8 | 0 | 0 | 1 | 1 | 54 |
| 9* | 2 | 0 | 1 | 1 | 50 |
| 10 | 1 | 0 | 0 | 1 | 1 |
| 11* | 2 | 5 | 1 | 3 | 1200 |
| 12 | 0 | 2 | 0 | 0 | 1 |
| 13 | 0 | 1 | 29 | 45 | 6800 |
| 14 | 0 | 0 | 23 | 0 | 270 |

*Inoculation

The observations summarized in Table VII indicated that disinfectant films prepared from the formulations of Table VI remain adherent, resistant to microbial contamination, and exhibit prolonged germicidal action after at least five inoculations and 14 water washes.

EXAMPLE 8

Effectiveness of Liquid Disinfectant Compositions as Germicidal Sprays

The liquid disinfectant compositions were prepared by combining the individual components as summarized in Table VIII.

TABLE VIII

| | Disinfectant Compositions | | | |
|---|---|---|---|---|
| | Formulation | | | |
| | I | | II | |
| Component | Grams | Wt % | Grams | Wt % |
| Copolymer Solution of Example 2. | 20.0 | 4.9 | 20.0 | 4.9 |
| Quat* | 8.0 | 2.0 | — | — |
| Phenol+ | — | — | 8.0 | 2.0 |

TABLE VIII-continued

| | Disinfectant Compositions | | | |
|---|---|---|---|---|
| | Formulation | | | |
| | I | | II | |
| Component | Grams | Wt % | Grams | Wt % |
| Isopropanol | 180.0 | 44.1 | 180.0 | 44.1 |
| Water | 200.0 | 49.0 | 200.0 | 49.0 |

*BTC 2125M.
+2-Benzyl-4-chlorophenol

Formulations I and II were evaluated as spray disinfectants on glass slides inoculated with S. aureus using a two minute exposure period by AOAC Method 4.033–4.035, *AOAC Methods of Analysis* (13th ed. 1980) at pages 63–64, the disclosure of which is incorporated by reference herein. All thirty inoculated slides sprayed with quat formulation I were negative for subsequent growth, as were 16 of 21 inoculated slides sprayed with phenolic formulation II. These results demonstrate that the film-forming liquid compositions of the present invention are effective to sanitize or substantially disinfect contaminated hard surfaces upon initial contact of the composition with the surface. As demonstrated by Example 7, the resultant films then act to impart prolonged residual antimicrobial properties to the treated surface, even after repeated water washes and microbial contamination.

The invention has been described with reference to various specific and preferred embodiments and techniques. However, it should be understood that many variations and modifications may be made while remaining within the spirit and scope of the invention.

What is claimed is:

1. A liquid antimicrobial film-forming composition, free of a polymer complex stabilized as a metal complex by the addition of a salt, said composition comprising a solution, in a volatile solvent, of an amount of a germicidal agent effective to impart prolonged antimicrobial properties and an effective film-forming amount of a water insoluble copolymer, said copolymer comprising:
   (a) about 50–99.5 mol-% of said copolymer of a monomer having an hydroxyl-containing functional group; and
   (b) about 0.50–50 mol-% of said copolymer of a monomer selected from the group consisting of an aromatic ester, a cycloalkyl ester, and ester mixtures thereof of an alpha, beta-unsaturated carboxylic acid.

2. A liquid disinfectant antimicrobial film-forming composition, free of polymer complex stabilized as a metal complex by the addition of a salt, said composition consisting essentially of a solution, in a volatile solvent, of an amount of a germicidal agent effective to impart prolonged antimicrobial properties and an effective film-forming amount of a water insoluble copolymer, said copolymer comprising:
   (a) about 50–95 mol-% of an hydroxyl-containing monomer selected from the group consisting of 2-hydroxyethyl-methacrylate, 2-hydroxypropyl-methacrylate, 3-hydroxypropyl-methacrylate, and diacetone acrylamide;
   (b) about 1–10 mol-% of said copolymer of an aromatic or cycloalkyl ester of an alpha, beta-unsaturated acid; and
   (c) about 1–10 mol-% of said copolymer of a $C_5$–$C_{20}$ alkyl ester or an alkyl ester of an alpha, beta-unsaturated acid.

3. The composition of claim 2 wherein the total concentration of the germicidal agent in the composition comprises about 0.25–20% by weight of the dissolved copolymer.

4. The composition of claim 1 wherein component (b) comprises about 1–90 mol-% of an alkyl or (alkoxy)alkyl ester of an alpha, beta-unsaturated acid in combination with a cycloalkyl ester or an aromatic ester of an alpha, beta-unsaturated acid.

5. The composition of claim 4 wherein the alkyl ester is a $C_5$–$C_{22}$ alkyl ester and the (alkoxy)alkyl ester is a ($C_1$–$C_4$) alkoxy ($C_1$–$C_4$) alkyl ester.

6. The composition of claim 1 wherein the monomer of component (a) comprises a hydroxyalkyl ester of an alpha, beta-unsaturated carboxylic acid.

7. The composition of claim 6 wherein the hydroxy alkyl ester comprises a hydroxyalkyl acrylate or a hydroxy alkyl methacrylate.

8. The composition of claim 1, wherein the alpha, beta-unsaturated carboxylic acid comprises acrylic acid, methacrylic acid or itaconic acid.

9. The composition of claim 1 wherein the copolymer comprises about 0.25–10% of the composition.

10. The composition of claim 1 wherein the germicidal agent comprises a phenolic compound or a quaternary ammonium salt.

11. The composition of claim 10 wherein the composition comprises the germicidal agent at a concentration of about 0.01–10%.

12. The composition of claim 1 wherein the germicidal agent comprises about 0.01–50% by weight of the dissolved copolymer.

13. The composition of claim 1 wherein the solvent comprises a $C_1$–$C_4$-alkanol or a mixture of water and a $C_1$–$C_4$ alkanol.

14. The composition of claim 2 wherein the film-forming copolymer is present at a concentration of about 0.5–5% of the composition.

15. The composition of claim 2 wherein the unsaturated acid is methacrylic acid, acrylic acid or itaconic acid.

16. The composition of claim 15 wherein the aromatic ester is a phenyl, benzyl or tetrahydrofurfuryl ester.

17. The composition of claim 2 wherein the cycloalkyl ester is a cyclohexyl, isobornyl or adamantyl ester.

18. The composition of claim 2 wherein the germicidal agent is present at a concentration of about 0.05–5% of the composition and is a germicidal phenolic compound or a quaternary ammonium salt.

19. The composition of claim 18 wherein the quaternary ammonium salt is a $C_{10}$–$C_{20}$-n-alkyl (dimethyl)benzyl ammonium salt.

20. The composition of claim 18 wherein the phenolic compound is 2-benzyl-4-chlorophenol.

21. The composition of claim 2 wherein the solvent is a water-alcohol mixture.

22. The composition claim 2 wherein the solvent is a lower(alkanol) and is present at a concentration of about 85% of the composition.

23. The composition of claim 2 wherein at least about 85% by weight of the composition is a mixture of alcohol and water.

24. The method for disinfecting and imparting prolonged germicidal properties to a hard porous or nonporous surface comprising coating said surface with the composition of claim 1, and removing the solvent from said coating to form a germicidal, water-resistant polymeric film thereupon.

25. The method of claim 24 wherein about 10–100 mg of the composition is applied per square inch of surface.

* * * * *